United States Patent [19]

Butler et al.

[11] Patent Number: 5,710,277
[45] Date of Patent: Jan. 20, 1998

[54] PROCESS FOR R (+) 1,2,3,6-TETRAHYDRO-4-PHENYL-1-[(3-PHENYL-3-CYCLOHEXEN-1-YL)METHYL]PYRIDINE, A CENTRAL NERVOUS SYSTEM AGENT

[75] Inventors: Donald Eugene Butler, Holland, Mich.; Jodette Gailey, Chicago, Ill.; Tung Van Le, Jenison, Mich.; William John Smith, III, Indianapolis, Ind.; David Juergen Wustrow, Ann Arbor, Mich.

[73] Assignee: Warner-Lambert Company, Morris Plains, N.J.

[21] Appl. No.: 304,074

[22] Filed: Sep. 12, 1994

[51] Int. Cl.$^6$ .................. C07D 211/02; C07C 69/76; C07C 65/32
[52] U.S. Cl. .................. 546/185; 560/59; 562/459
[58] Field of Search .................. 546/185; 560/59; 562/459

[56] References Cited

U.S. PATENT DOCUMENTS 5,314,896  5/1994  Caprathe et al. .................. 514/332

FOREIGN PATENT DOCUMENTS 1189982  10/1959  France .
9310092  5/1993  WIPO .

OTHER PUBLICATIONS

Chemical Abstract vol. 109 #170,683, Salvador, et al, 1987, "A Novel Application of Cinchona Alkaloids as Chiral Auxiliaries".
Chemical Abstract vol. 112 #119,212, Coors et al, 1989, "New Chiral Phases for Racemate Resolution Prepared by Azo-Coupling of Quinine Alkaloids".
PCT International Search Report, PCT/US 95/09511.
Bulletin de la Societe Chimique de France, No. 10, pp. 1354–1359 (1957), Julia and Bonnet.
*Journal of Medicinal Chemistry*, vol. 37, No. 21, pp. 3523–3533 (1994), Wright et al.
Johnson, S.J., et al., 206th National Meeting, American Chemical Society, Chicago, Illinois, Aug. 1993, MEDI–171.
*Tetrahedron Letters*, vol. 35, No. 1 pp. 61–64 (1994), Wustrow, D.J., et al.
Wright, J., et al., 206th National Meeting, American Chemical Society, Chicago, Illinois, Aug. 1993, MEDI–22.
Downing, D.M., et al., 208th National Meeting American Chemical Society, Washington, D.c., Aug. 1994, MEDI–178.
Downing, D.M., et al., 206th National Meeting American Chemical Society, Chicago, Illinois, Aug. 1993, MEDI–173.
Wise, L.D., et al., 208th National Meeting American Chemical Society, Washington, D.C., Aug. 1994, MEDI–266.

*Primary Examiner*—C. Warren Ivy
*Assistant Examiner*—Raymond Covington
*Attorney, Agent, or Firm*—Francis J. Tinney

[57] ABSTRACT

An improved process for the preparation of R(+)1,2,3,6-tetrahydro-4-phenyl-1-[(3-phenyl-3-cyclohexen-1-yl) methyl]pyridine by a novel synthesis is described where 5-oxo-3-phenyl-3-cyclohexene-carboxylic acid is converted in five operations to the desired product, as well as processes for the resolution of 5-oxo-3-phenyl-3-cyclohexenecarboxylic acid using cinchonidine to afford (S)5-oxo-3-phenyl-3-cyclohexenecarboylic acid or α-chymotrypsin to selectively hydrolyze n-butyl 5-oxo-3-phenyl-3-cycohexenecarboxylate to afford (S)5-oxo-3-phenyl-3-cyclohexenecarboxylic acid as well as other valuable intermediates used in the processes.

39 Claims, No Drawings

PROCESS FOR R (+) 1,2,3,6-TETRAHYDRO-4-PHENYL-1-[(3-PHENYL-3-CYCLOHEXEN-1-YL)METHYL]PYRIDINE, A CENTRAL NERVOUS SYSTEM AGENT

BACKGROUND OF THE INVENTION

U.S. Pat. No. 5,314,896, which is herein incorporated by reference, discloses a series of central nervous system agents. It also discloses the pharmaceutically acceptable salts thereof.

The compounds disclosed in the above United States patent are useful as dopaminergic agents. As dopaminergic agents, the compounds are useful for treating psychoses such as schizophrenia and hyperprolactinemia-related conditions such as galactorrhea, amenorrhea, menstrual disorders, and sexual dysfunction. They are also useful as antihypertensive agents. Particularly valuable as an antipsychotic agent is R(+)1,2,3,6-tetrahydro-4-phenyl-1-[(3-phenyl-3-cyclohexen-1-yl)methyl]-pyridine.

The methods disclosed in U.S. Pat. No. 5,314,896, while extremely inefficient in terms of overall yield and time expenditures, are very useful in producing a wide array of substitutions on the aryl group on the cyclohexane ring and varying the substitutions on the amino portion of the molecule. As a consequence of the dehydration step in the synthetic process, that route also produced 2,3-cyclohexene isomers which could be chromatographically separated for biological testing. In addition, preparation of the salt of 1,2,3,6-tetrahydro-4-phenyl-1-[(3-phenyl-3-cyclohexen-1-yl)methyl]pyridine with (R)(−)1,1-binaphthyl-2,2'-diyl hydrogen phosphate, followed by recrystallization and liberation of the free base, yielded R(+)1,2,3,6-tetrahydro-4-phenyl-1-[(3-phenyl-3-cyclohexen-1-yl)methyl]pyridine for biological assessment.

In addition, a number of other methods have been disclosed for the preparation of R(+)1,2,3,6-tetrahydro-4-phenyl-1-[(3-phenyl-3-cyclohexen-1-yl)methyl]-pyridine and related compounds. Thus, Johnson S. J., et al., 206th National Meeting American Chemical Society, Chicago, Ill., August 1993, MEDI-171 disclosed several syntheses of this compound. In one procedure, Johnson, et al., employs an intramolecular Wittig cyclization in which the starting material is a known irritant and lachrymator and the procedure requires the resolution of the intermediate racemic ene-acid with greater than 50% loss of material. Additionally, Johnson, et al., and Wustrow, D., et al., *Tetrahedron Letters* 35:61 (1994) disclosed a ketone deoxygenation procedure using triethylsilylhydride and lithium perchlorate in diethyl ether reagents, which are not amenable to large-scale synthesis. Wright, J., et al., 206th National Meeting American Chemical Society, Chicago, Ill., August 1993, MEDI, disclosed a route to the desired compound which requires resolution of an intermediate which results in greater than 50% loss of the desired intermediate. Downing, D. M., et al., 208th National Meeting American Chemical Society, Washington, D.C., August 1994, MEDI-178 and Downing, D. M., et al., 206th National Meeting American Chemical Society, Chicago, Ill., August 1993 MEDI-173 disclosed various routes to the desired compound which involve multiple chromatographies and resolutions that afford less than 50% of the step that is resolved. Finally, Wise, L. D., et al., 208th National Meeting American Chemical Society, Washington, D.C., August 1994, MEDI-266 disclosed a route for the desired compound which did not discuss resolution to obtain R(+)1,2,3,6-tetrahydro-4-phenyl-1-[(3-phenyl-3-cyclohexen-1-yl)-methyl]pyridine.

These synthetic methods allowed the structure activity limits of biological utility to be established. However, they are not amenable to a large-scale industrial process since they involve multiple chromatographies, inefficient resolution of intermediates, utilize hazardous reagents, and produce a low overall yield.

The object of the present invention is an improved process for preparing R(+)1,2,3,6-tetrahydro-4-phenyl-1-[(3-phenyl-3-cyclohexen-1-yl)methyl]pyridine described above by using a novel synthesis. Further, we have unexpectedly found that the particularly valuable dopaminergic agent R(+)1,2,3,6-tetrahydro-4-phenyl-1-[(3-phenyl-3-cyclohexen-1-yl)methyl]pyridine maleate can be prepared from novel intermediates in fewer steps without chromatography, without losing greater than 50% of material by resolution of a RS mixture of 1,2,3,6-tetrahydro-4-phenyl-1-[(3-phenyl-3-cyclohexen-1-yl)methyl]pyridine and higher yields than the previous methods. Moreover, the present method proceeds from inexpensive starting materials and is amenable to large-scale synthesis.

SUMMARY OF THE INVENTION

Accordingly, a first aspect of the present invention is an improved process for the preparation of the compound of Formula I

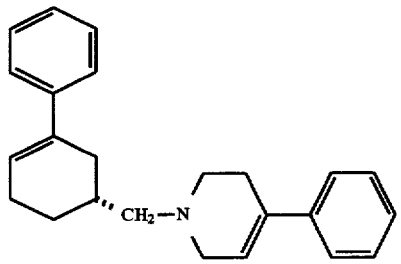

and pharmaceutically acceptable salts thereof which comprises:

Step (a) treating the racemic compound of Formula VIII

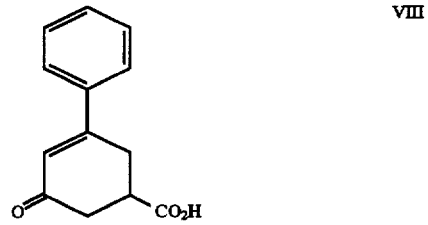

with cinchonidine in a solvent to afford the compound of Formula VII

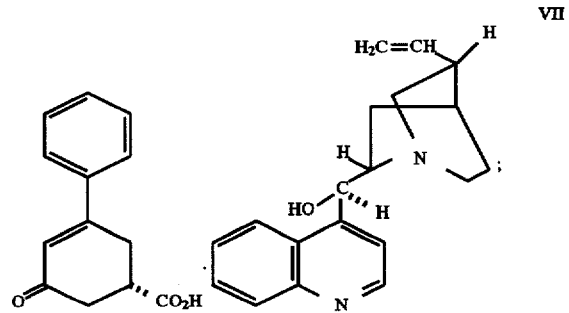

Step (b) treating the compound of Formula VII with a base in a solvent to afford after acidification the compound of Formula VI

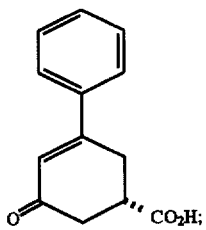

Step (c) treating the compound of Formula VI with the compound of Formula V

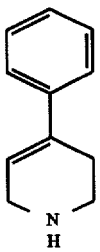

in the presence of a coupling reagent and a solvent to afford the compound of Formula IV

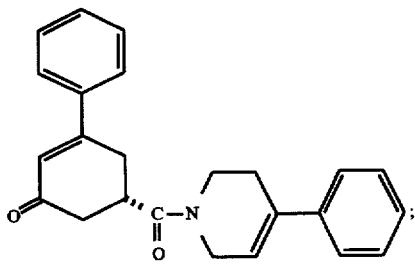

Step (d) treating the compound of Formula IV with a reducing reagent in a solvent to afford a mixture of compounds of Formula IIIa and Formula IIIb

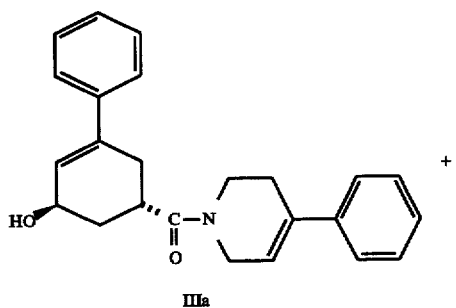

+

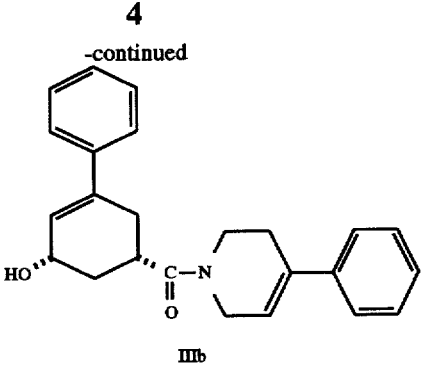

Step (e) treating the mixture of compounds of Formula IIIa and Formula IIIb with a mixture of zinc chloride, and sodium cyanoborohydride in a solvent followed by a solution of a carboxylic acid in a solvent to afford the compound of Formula II

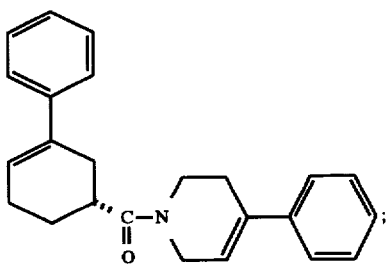

Step (f) treating the compound of Formula II with a metal hydride reducing agent in a solvent to afford the compound of Formula I;

Step (g) and, if desired, converting the resulting compound of Formula I to a corresponding pharmaceutically acceptable acid addition salt by conventional means, and if so desired, converting the corresponding pharmaceutically acceptable acid addition salt to a compound of Formula I by conventional means.

A second aspect of the present invention is a process for the preparation of the compound of Formula VI

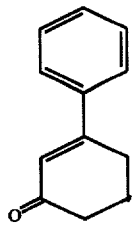

which comprises:
Step (a) treating the racemic compound of Formula VIII

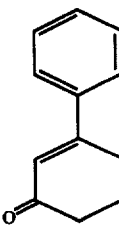

with cinchonidine in a solvent to afford the compound of Formula VII

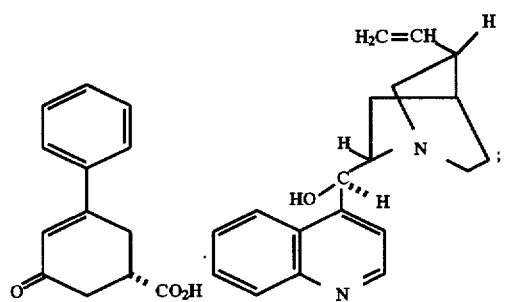

Step (b) treating the compound of Formula VII with a base in a solvent to afford after acidification the compound of Formula VI.

A third aspect of the present invention is a process for the preparation of the compound of Formula VI

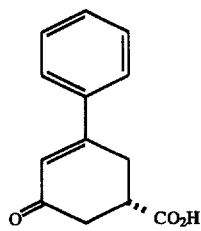

which comprises treating the racemic compound of Formula IX

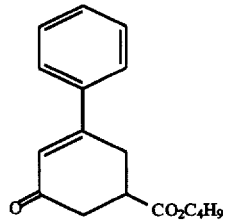

in a solvent at about pH 5 with α-chymotrypsin to afford after separation of unreacted ester and acidification the compound of Formula VI.

A fourth aspect of the present invention is a process for the preparation of the compound of Formula II

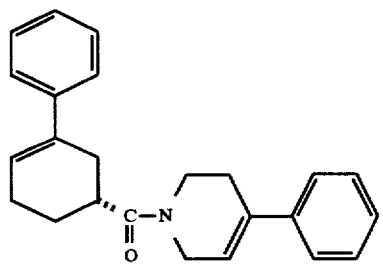

which comprises:

Step (a) treating the racemic compound of Formula VIII

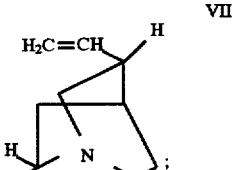

with cinchonidine in a solvent to afford the compound of Formula VII

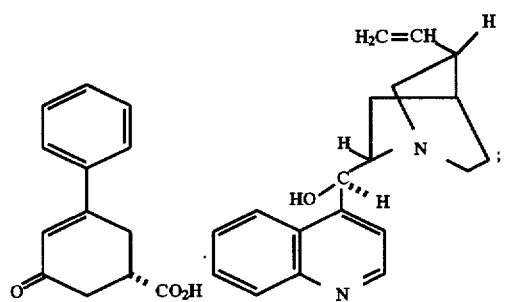

Step (b) treating the compound of Formula VII with a base in a solvent to afford after acidification the compound of Formula VI

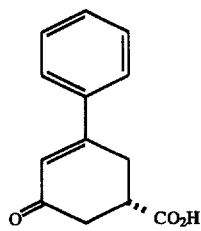

Step (c) treating the compound of Formula VI with the compound of Formula V

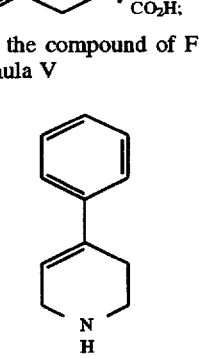

in the presence of a coupling reagent and a solvent to afford the compound of Formula IV

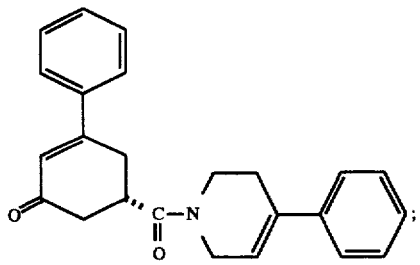

Step (d) treating the compound of Formula IV with a reducing reagent in a solvent to afford a mixture of compounds of Formula IIIa and Formula IIIb

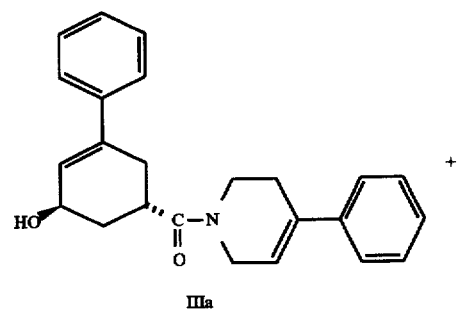

IIIa

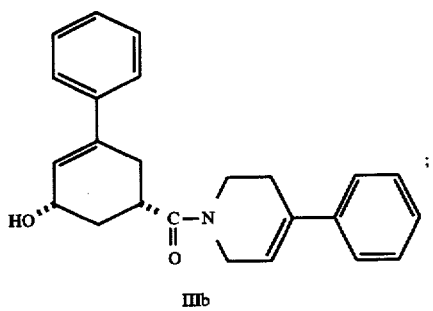

IIIb

Step (e) treating the mixture of compounds of Formula IIIa and Formula IIIb with a mixture of zinc chloride, and sodium cyanoborohydride in a solvent followed by a solution of a carboxylic acid in a solvent to afford the compound of Formula II.

A fifth aspect of the present invention is a process for the preparation of the compounds of Formula IIIa and Formula IIIb

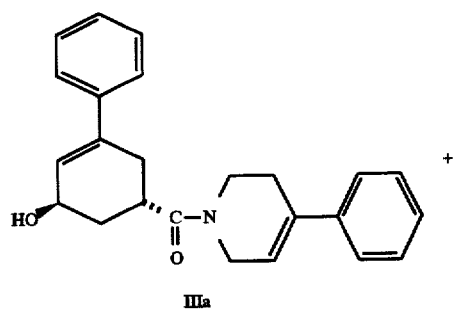

IIIa

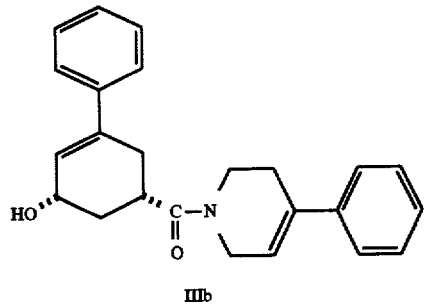

IIIb which comprises:

Step (a) treating the racemic compound of Formula VIII

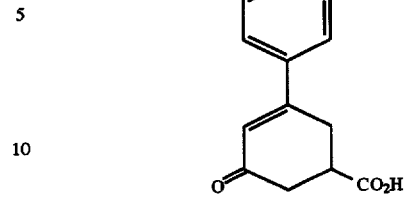

VIII with cinchonidine in a solvent to afford the compound of Formula VII

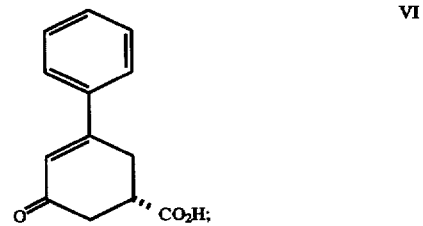

VII

Step (b) treating the compound of Formula VII with a base in a solvent to afford after acidification the compound of Formula VI

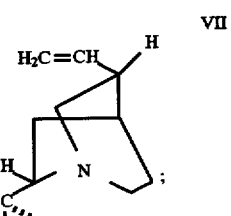

VI

Step (c) treating the compound of Formula VI with the compound of Formula V

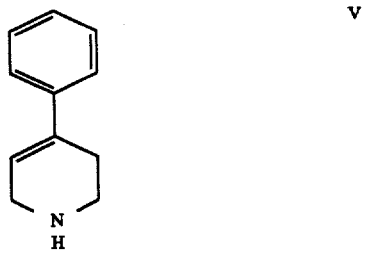

V in the presence of a coupling reagent and a solvent to afford the compound of Formula IV

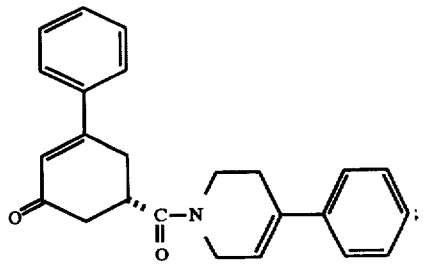

IV

Step (d) treating the compound of Formula IV with a reducing reagent in a solvent to afford a mixture of compounds of Formula IIIa and Formula IIIb.

A sixth aspect of the present invention is a process for the preparation of the compound of Formula IV

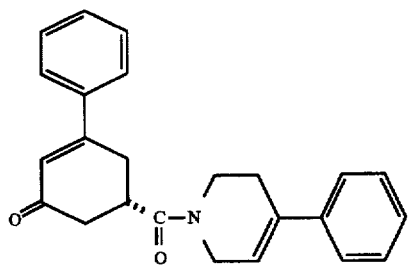

IV which comprises:

Step (a) treating the racemic compound of Formula VIII

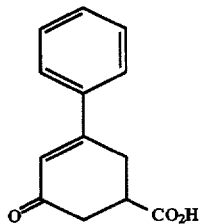

VIII with cinchonidine in a solvent to afford the compound of Formula VII

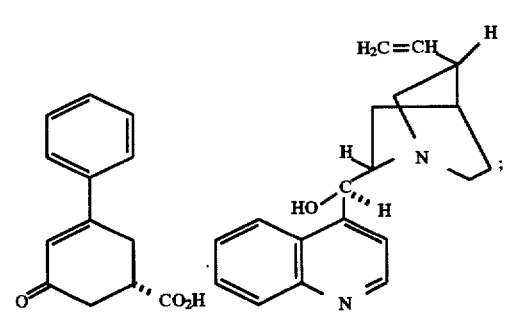

VII

Step (b) treating the compound of Formula VII with a base in a solvent to afford after acidification the compound of Formula VI

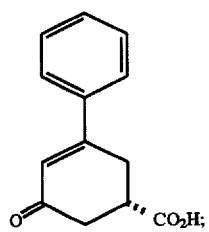

VI

Step (c) treating the compound of Formula VI with the compound of Formula V

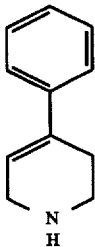

V in the presence of a coupling reagent and a solvent to afford the compound of Formula IV.

A seventh aspect of the present invention is a novel intermediate of Formula IIIa or Formula IIIb

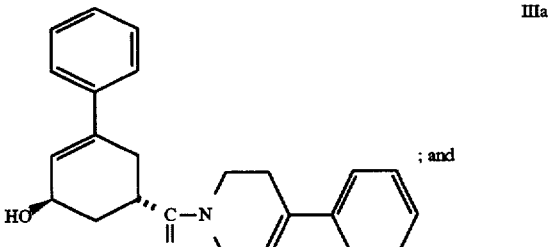

IIIa

; and

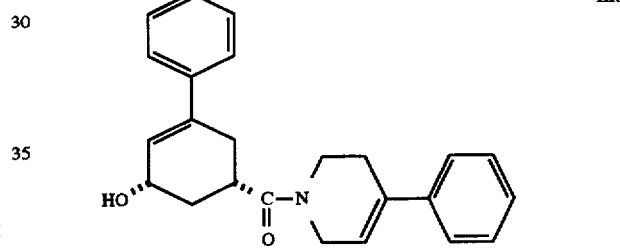

IIIb which are useful in the preparation of the compound of Formula II, which in turn is useful in the preparation of the antipsychotic compound of Formula I.

An eighth aspect of the present invention is the novel intermediate of Formula IV

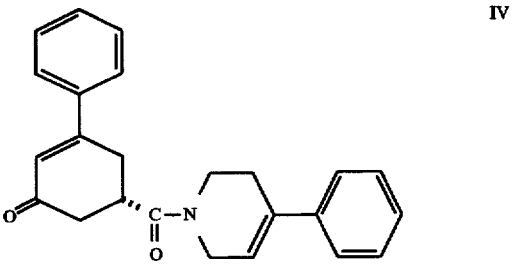

IV which is useful in the preparation of a compound of Formula IIIa or Formula IIIb, which in turn is useful in the preparation of the compound of Formula II, which in turn is useful in the preparation of the antipsychotic compound of Formula I.

A ninth aspect of the present invention is the novel intermediate of Formula VI

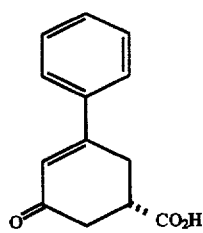
VI which is useful in the preparation of the compound of Formula IV, which in turn is useful in the preparation of a compound of Formula IIIa or Formula IIIb, which in turn is useful in the preparation of the compound of Formula II, which in turn is useful in the preparation of the antipsychotic compound of Formula I.

An tenth aspect of the present invention is the novel intermediate of Formula VII

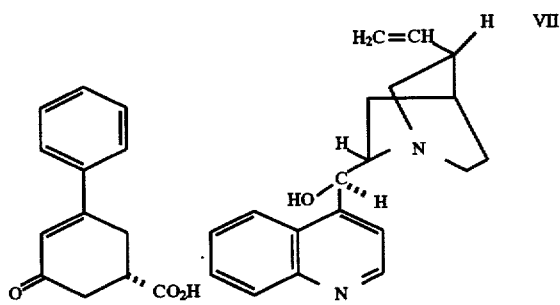
VII

An eleventh aspect of the present invention is the novel intermediate of Formula IX

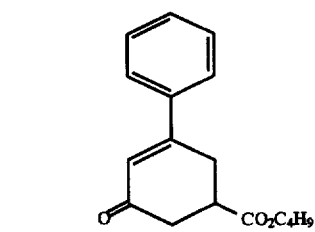
IX which is useful in the preparation of the compound of Formula VI, which in turn is useful in the preparation of the compound of Formula IV, which in turn is useful in the preparation of a compound of Formula IIIa or Formula IIIb, which in turn is useful in the preparation of the compound of Formula II, which in turn is useful in the preparation of the antipsychotic compound of Formula I.

DETAILED DESCRIPTION OF THE INVENTION

In this invention, the term "alkyl" means a straight or branched hydrocarbon group having from 1 to 6 carbon atoms and includes, for example, methyl, ethyl, n-propyl, isopropyl, n-butyl, isobutyl, tertiary-butyl, n-pentyl, tertiary-amyl, n-hexyl, and the like.

"Alkali metal" is a metal in Group IA of the periodic table and includes, for example, lithium, sodium, potassium, and the like.

"Mineral acid" is a strong acid that includes, for example, hydrochloric acid, hydrobromic acid, sulfuric acid, and the like.

"Carboxylic acid" is an organic acid that includes, for example, acetic acid, propanoic acid, butyric acid, pivalic acid, and the like.

"Cation Borohydride" is a reducing agent that includes lithium borohydride, sodium borohydride, potassium borohydride, and the like.

"Metal hydride reducing agent" is a reducing agent that reduces carboxylic acid amides that includes lithium aluminum hydride, sodium bis(2-methoxyethoxy)-aluminum hydride, and the like.

A "still" is a reaction system with a condenser that allows distillation of a solvent.

A "reactor" is a reaction system with a condenser that returns solvent directly into the reaction system.

The compound of Formula I is capable of further forming pharmaceutically acceptable acid addition salts. All of these forms are within the scope of the present invention.

Pharmaceutically acceptable acid addition salts of the compound of Formula I include salts derived from nontoxic inorganic acids such as hydrochloric, nitric, phosphoric, sulfuric, hydrobromic, hydriodic, phosphorous and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate (see, for example, Berge S. M., et al., "Pharmaceutical Salts," *Journal of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

As previously disclosed in U.S. Pat. No. 5,314,896 the compound of Formula I is useful as a dopaminergic agent as determined by methodology known in the art. The compound of Formula I possesses activity representative of an antipsychotic agent.

The process of the present invention in its first aspect is a new, improved, economical, and commercially feasible method for preparing the antipsychotic agent of Formula I. The process of the present invention is outlined in Scheme I.

SCHEME I
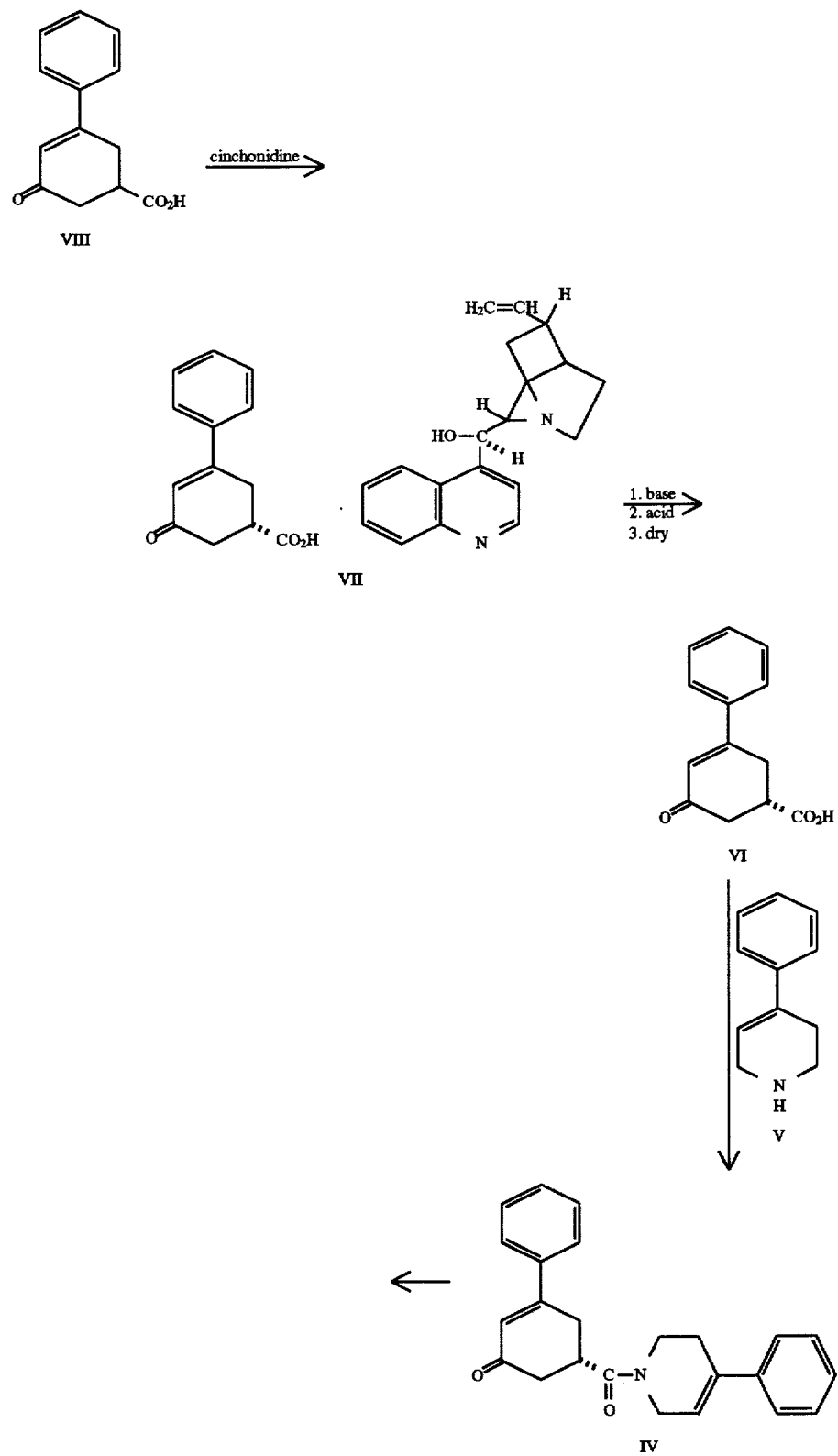

-continued
SCHEME I

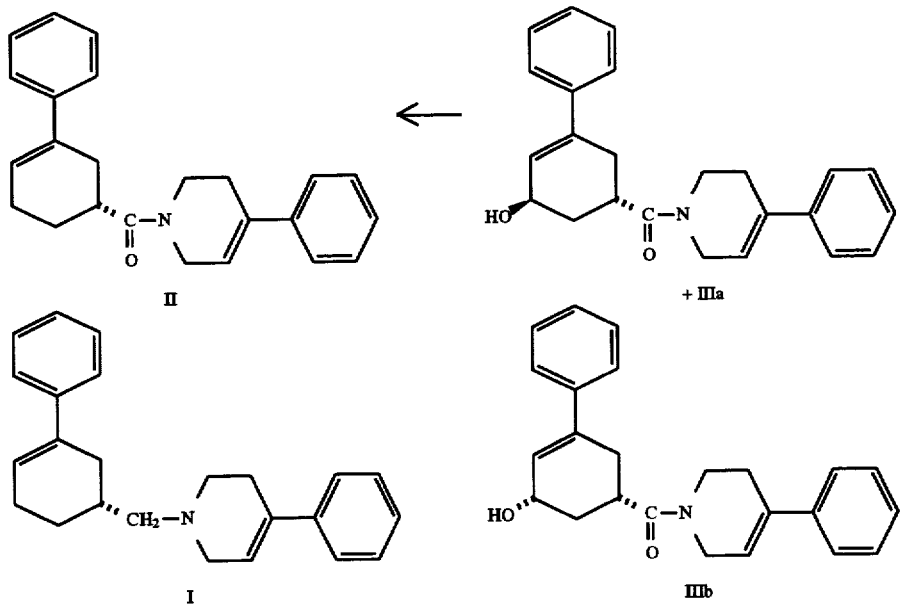

The compound of Formula VIII is prepared from benzoylacrylic acid using a modification of the methodology described by S. Julia and Y. Bonnet, *Bull. Soc. Chim.*, 1354–1364 (1957).

Thus, the compound of Formula VIII is dissolved in a solvent, for example, an alcohol of from 1 to 4 carbon atoms such as, for example, methanol, ethanol, isopropanol, n-butanol, and the like at about 25° C. to about the reflux temperature of the solvent, and the resulting solution is treated with a suspension or solution of cinchonidine in the same solvent to afford the cinchonidine salt of Formula VII. If desired, the salt is recrystallized to higher enantiomeric purity from an alcohol of from 1 to 4 carbon atoms such as, for example, methanol, ethanol, isopropanol, n-butanol, and the like. The compound of Formula VII is dissolved in a solvent, for example, an alcohol of from 1 to 4 carbon atoms such as, for example, methanol, ethanol, isopropanol, n-butanol, and the like at a temperature of about 25° C. to about the reflux temperature of the solvent. The suspension or solution is treated with an aqueous solution of an alkali metal hydroxide such as, for example, sodium hydroxide, potassium hydroxide, and the like to form the alkali metal salt of the compound of Formula VI. The alcohol is removed by vacuum distillation and partially replaced with water, and the crystalline cinchonidine is recovered by filtration. The aqueous filtrate containing the alkali metal salt of the compound of Formula VI is treated with an excess of a mineral acid solution, cooled, and filtered to yield the compound of Formula VI. The R enantiomer can be recovered and racemized to Example A using standard methodology. The compound of Formula VI is dried in vacuo at about 55° C. to about 80° C. for about 24 to about 48 hours to a water content of less than 0.2%.

The compound of Formula VI is treated with a coupling reagent, for example, an acid activating reagent or reagents such as carbonyl diimidazole or 1-(3-dimethylaminopropyl)-3-ethylcarbodiimide, 1-hydroxybenzotriazole hydrate, and triethyl amine and the like. The activated acid is treated with the compound of Formula V, 4-phenyl-1,2,3,6-tetrahydropyridine or 4-phenyl-1,2,3,6-tetrahydropyridine hydrochloride and triethylamine in an inert solvent such as, for example, acetonitrile, tetrahydrofuran, and the like. The amide formation is performed at about 0° C. to about the reflux temperature of the solvent for about 3 to about 24 hours. The reaction is quenched by adding an aqueous solution of an alkali metal bicarbonate, carbonate or hydroxide, for example, sodium bicarbonate, sodium carbonate, sodium hydroxide, and the like. The compound of Formula IV is extracted into an inert water immiscible solvent such as, for example, toluene, diethyl ether, tert-butyl methyl ether, and the like. The solution is washed with dilute mineral acid to remove any unreacted basic materials. The solution is concentrated, and the solvent is replaced with an alcohol of from 1 to 4 carbon atoms such as, for example, methanol, ethanol, isopropanol, n-butanol, and the like. The solution is cooled to about −5° C. to about 25° C., and the compound of Formula IV is isolated by filtration. The compound of Formula IV may be dried in vacuum if storage is desired or used damp in the next reaction.

The compound of Formula IV is dissolved in a solvent, for example, an alcohol of from 1 to 4 carbon atoms such as, for example, methanol, ethanol, isopropanol, n-butanol, and the like or aqueous mixtures thereof, and a reducing reagent, for example, a cation borohydride such as, for example, sodium borohydride and the like is added as a solid or a solution. The mixture is agitated for about 3 to 24 hours at a temperature between about 15° C. and about 35° C. An aqueous solution of ammonium chloride is added and the mixture is cooled to about 0° C. to about 5° C. A mixture of compounds of Formula IIIa and Formula IIIb is isolated by filtration and dried in vacuo at about 25° C. to about 55° C. to a water content of less than 0.2%.

The compounds of Formula IIIa and Formula IIIb are mixed with anhydrous zinc chloride, sodium cyanoborohydride, and an inert solvent such as, for example, hexane or heptane and the like. A solution of a carboxylic acid such as, for example, acetic acid, propanoic acid, butyric acid, pivalic acid, and the like in an inert solvent such as, for example, hexane, heptane, tetrahydrofuran and the like is added at a reaction temperature of about 25° C. to about 35°

C. The mixture is agitated for about 6 to about 24 hours, and an aqueous solution of ammonium chloride is added. The compound of Formula II is filtered in an enclosed filter, and the solid is washed with water. The solid is dissolved in a solvent such as, for example, tetrahydrofuran, tert-butyl methyl ether, or a heated alcohol of from 1 to 4 carbon atoms such as, for example, methanol, ethanol, isopropanol, n-butanol, and the like to remove it from the enclosed filter. The solvent is removed by distillation and if not an alcohol, the solvent is replaced by an alcohol of from 1 to 4 carbon atoms such as, for example, methanol, ethanol, isopropanol, n-butanol, and the like. The solution is cooled to about 0° C. to about 5° C., and the compound of Formula II is isolated by filtration. The compound of Formula II is dried in vacuo to a solvent content of less than 0.1%.

The compound of Formula II is suspended or dissolved in an inert solvent such as, for example, tetrahydrofuran, diethyl ether, tert-butyl methyl ether, and the like and treated with a metal hydride reducing agent such as, for example, lithium aluminum hydride and the like in an inert solvent such as, for example, tetrahydrofuran and the like at a temperature of about 25° C. to about 55° C. for about 3 to about 4 hours. The solution is cooled to about 20° C. to about 25° C. A measured amount of water in tetrahydrofuran is added followed by a measured amount of saturated sodium sulfate solution in water. The resulting slurry is heated to about 50° C. to about 60° C., and the inorganic salts are removed by filtration. The inert solvent is distilled in vacuo and is replaced by an alcohol of from 1 to 4 carbon toms such as, for example, methanol, ethanol, isopropanol, n-butanol, and the like. Acetonitrile can also be used. The solvent is distilled in vacuo and again replaced by an alcohol of from 1 to 4 carbon atoms such as, for example, methanol, ethanol, isopropanol, n-butanol, and the like. The solution is cooled to about 0° C. to about 5° C. and agitated for at least 2 hours. The compound of Formula I is isolated by filtration.

The compound of Formula I is dissolved in a minimum amount of an alcohol of from 1 to 4 carbon atoms such as, for example, methanol, ethanol, isopropanol, n-butanol, and the like at about the reflux temperature of the solvent. The solution is treated with a pharmaceutically acceptable acid such as, for example, a maleic acid suspension or solution in an alcohol of from 1 to 4 carbon atoms such as, for example, methanol, ethanol, isopropanol, n-butanol, and the like. The solution is cooled to about 0° C. to about 5° C. and agitated for at least 2 hours. The maleic acid salt of the compound of Formula I is isolated by filtration. The maleic acid salt of the compound of Formula I is dried in vacuo at about 25° C. to about 35° C. for about 16 to about 24 hours.

The process of the present invention in its third aspect is a new, improved, economical, and commercially feasible alternate method for preparing the compound of Formula VI. The racemic compound of Formula IX

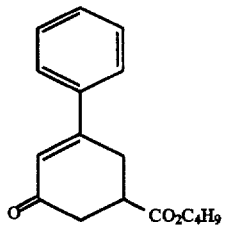

IX in a solvent such as, for example, water, is brought to a pH of about five using an acid such as, for example, dilute hydrochloric acid and the like. The mixture is subsequently treated with α-chymotrypsin, and the pH is maintained at about five by the addition of a base such as, for example, dilute sodium hydroxide and the like at about ambient temperature for about 2.09 days. The reaction is completed when the consumption of base is at about 90% to about 100% of the theoretical amount needed to hydrolyze 50% of the racemic ester of Formula IX. Preferably, the reaction is carried out in water at about pH 5 with dilute hydrochloric acid and dilute sodium hydroxide at about ambient temperature for about 2.09 days. The unreacted ester is extracted and the alkali metal salt of the acid is treated with acid to afford the compound of Formula VI.

The compound of Formula IX is obtained from the compound of Formula VIII

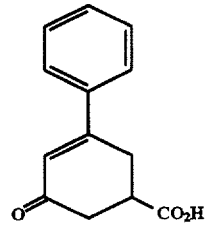

VIII by reaction with n-butanol in the presence of an acid such as, for example, sulfuric acid and the like at about room temperature to about 100° C. for about 18 hours to about 24 hours to afford the compound of Formula IX. Preferably, the reaction is carried out with sulfuric acid at about 50°–55° C. for about 22 hours.

The following nonlimiting example illustrates the inventors' preferred method for preparing the compound of the invention.

EXAMPLE 1

R(+)1,2,3,6-Tetrahydro-4-phenyl-1-[(3-phenyl-3-cyclohexen-1-yl)methyl]pyridine Maleate

Step A

Preparation of (S)5-oxo-3-phenyl-3-cyclohexenecarboxylic Acid

Method A

Cinchonidine Procedure

A 400 L still is charged with 50.0 kg (231.4 mol) of 5-oxo-3-phenyl-3-cyclohexenecarboxylic acid (Example A, Formula VIII) and 175 L of isopropanol, and the agitator is started. The material in the still is heated to 70°–75° C. and the solid goes into solution. A reactor is charged with 50.0 kg (170 mol) of cinchonidine and 275 L of isopropanol, and the agitator is started. The material in the reactor is heated to 50°–75° C. to afford a mobile slurry that is readily transfered. The suspension/solution is transferred from the reactor into the still containing the solution of 5-oxo-3-phenyl-3-cyclohexenecarboxylic acid. The reactor is charged with 31 L of isopropanol as a wash. The wash in the reactor is transferred into the still. Complete solution is obtained at this point. The contents of the still are cooled to 50°–55° C. over about 1 hour. The heat transfer medium (HTM) control on the still is set at 50° C. for at least 2 hours. The HTM control on the still is set at 40° C. for at least 1 hour. The HTM control on the still is set at 25° C. for at least 10 hours. The contents of the still are cooled to 0°–5° C. and are agitated for at least 2 hours. The solid product is filtered from the still onto a centrifuge, and the mother liquor is directed to a "recovery" reactor. This is for later recovery of cinchonidine and the (R)5-oxo-3-phenyl-3-cyclohexenecarboxylic acid. The still is charged with 41 L of isopropanol which is used to wash the filter-cake. The wash is directed to the "recovery" reactor. A 200 L still is charged with the product wet cake from the centrifuge. The 200 L still is charged with 50 kg of ethanol, 2B. The mixture is agitated and heated to reflux for about 15 minutes. The agitation is slowed, and the HTM control is set at 25° C. Agitation is continued for at least 8 hours. The contents of the still are cooled to 0°–5° C. and agitated for at least 2 hours. The solid product in the 200 L still is filtered on a centrifuge, and the mother liquor is directed to the "recovery" reactor. The 200 L still is charged with 4 kg of ethanol, 2B, which is used to wash the filter-cake. The wash is directed to the "recovery" reactor. Approximately 10 g of the solid is taken from the centrifuge, and the free acid is isolated by acidifying with hydrochloric acid, extracting twice with ethyl acetate, and concentrating the extract on a rotary evaporator. The resulting product is analyzed by chiral HPLC. If the S:R ratio is not >99:1 recrystallizating from ethanol, 2B will reach that level.

The salt from the centrifuge is charged to a 400 L still with 67 kg of methanol, and the agitator is started. A solution of 3.75 kg of sodium hydroxide, 50% in 40 L of water is charged to the still. The mixture is agitated for about 1 hour at 20°–25° C., and the still is charged with 120 L of water. The alcohol is agitated and vacuum distilled at a temperature of 30°–35° C. until the rate of distillation markedly slows. The contents are cooled to 20°–25° C. The vacuum is broken with nitrogen, and the distillate is discarded. The recovered solid cinchonidine in the still is filtered onto a centrifuge. The filtrates are directed to a reactor. The recovered cinchonidine is washed on the centrifuge with 20 L of water, and the wash is directed to the reactor. The water wet recovered cinchonidine is transferred to a vacuum tray dryer and dried at 35°±5° C. for at least 24 hours using the best available vacuum. The recovered cinchonidine can be reused. The sodium salt of the product solution in the reactor is treated with 13 kg of hydrochloric acid 37%, CP with agitation. The pH of the suspension is checked with pH paper. The pH should be 1.5 to 2.0. If the pH is higher than 2.0, additional hydrochloric acid 37%, CP is added. The resulting suspension in the still is agitated for around 1 hour and cooled to 5°–10° C. The (S)5-oxo-3-phenyl-3-cyclohexenecarboxylic acid in the still is filtered onto a centrifuge. The filtrate is discarded. The still is charged with 20 L water and it is used to wash the filter-cake. The wash is discarded. The water wet (S)5-oxo-phenyl-3-cyclohexenecarboxylic acid is transferred to a vacuum tray dryer and dried at 65° C.±5° C. for at least 24 hours using the best available vacuum. The yield of (S)5-oxo-3-phenyl-3-cyclohexenecarboxylic acid is 20 kg as a white to pale yellow solid; mp 111°–113° C. (uncorrected).

200 MHz $^1$H NMR (CDCl$_3$): δ2.3–2.95 (m, 4H), 2.96–3.45 (m, 3H), 6.45 (s, 1H), 7.25–7.65 (m, 5H), 10.0–10.8 (br.s, 1H).

| Chiral Assay (HPLC): | S enantiomer 99.24%. retention time = 26.9 minutes R enantiomer 0.76%, retention time = 20.9 minutes |
|---|---|
| Chiral HPLC Conditions: | |
| Column | Chiralpak AD, 250 × 4.6 mm |
| Flow Rate: | 1.0 mL/minute |
| Mobile Phase: | 900 hexane/100 isopropanol/ |

| | |
|---|---|
| | 1 formic acid (v/v) |
| Wavelength: | 254 nm |
| Volume Injected: | 20 μL |
| Sample Concentration: | ~10.0 mg/10 mL in isopropanol |
| Retention Time: | S enantiomer ~25–27 minutes |
| | R enantiomer ~20–21 minutes |

Store the column in 900 hexane/100 isopropanol (v/v) after use.

The filtrates from the "recovery" reactor are transferred to a still. The still is charged with 11.2 kg of sodium hydroxide, 50% in 100 L of water with agitation. The solvents are agitated and vacuum distilled at a temperature of 30°–35° C. until the rate of distillation markedly slows. The contents of the still are cooled to 20°–25° C., and the vacuum is broken with nitrogen. The distillate is discarded. The still is charged with 50 L of water, the recovered cinchonidine in the still is filtered onto a centrifuge, and the mother filtrate is directed to a reactor. The recovered cinchonidine is washed on the centrifuge with 20 L of water, and the wash is directed to the reactor. The water wet recovered cinchonidine is transferred to a vacuum tray dryer and dried at 35°±5° C. for at least 24 hours using the best available vacuum. The filtrates (solution of the sodium salt of mostly (R)5-oxo-3-phenyl-3-cyclohexenecarboxylic acid) in the reactor is transferred to a still. The still is charged with 15 kg of hydrochloric acid 37%, CP with agitation. The resulting suspension in the still is agitated for around 1 hour and cooled to 5°–10° C. The solid (R)5-oxo-3-phenyl-3-cyclohexenecarboxylic acid in the still is filtered onto a centrifuge. The filtrate is discarded. The still is charged with 20 L water, and it is used to wash the filter-cake. The filtrate is discarded. The water wet (R)5-oxo-3-phenyl-3-cyclohexenecarboxylic acid is transferred to a vacuum tray dryer and dried at 80°±5° C. for at least 24 hours using best available vacuum. This can be racemized to Example A, Formula VIII, using standard methodology.

Method B

α-chymotrypsin Procedure

One gram of n-Butyl 5-oxo-3-phenyl-3-cyclohexenecarboxylate (Example B) is placed in a 250 mL round-bottom flask equipped with a mechanical stirrer. Approximately 80 mL of water is added to the ester, and the mixture is stirred. The mixture is brought to a pH of 5.0 using dilute hydrochloric acid. To this solution, 0.1 g (~10% by weight) of α-chymotrypsin is added and rinsed in with 20 mL of water. The pH of the reaction mixture is maintained at pH 5 by the addition of a dilute sodium hydroxide solution via a laboratory pH control system. The reaction is run at ambient temperature. The reaction is stopped after 2.09 days, e.g., when the consumption of base is at 90–100% of the theoretical amount needed to hydrolyze 50% of the racemic mixture.

The ratio of (R) ester to (S) ester is 94:6.

The desired (S)5-oxo-3-phenyl-3-cyclohexene-carboxylic acid is obtained by acidification with dilute hydrochloric acid. The solid is filtered and dried in vacuo at 80°±5° C. for at least 24 hours using best available vacuum.

Step B

Preparation of (S)1,2,3,6-tetrahydro-1-[(5-oxo-3-phenyl-3-cyclohexenyl)carbonyl]-4-phenylpyridine Method A A 400 L still is charged with 6.0 kg (27.8 mol) of (S)5-oxo-3-phenyl-3-cyclohexenecarboxylic acid, 4.1 kg (30.3 mol) of 1-hydroxybenzotriazole hydrate, 7.0 kg (31.6 mol) of 1-(3-dimethylaminopropyl)-3-ethyl-carbodiimide·HCl, 6.2 kg (33.4 mol) of 4-phenyl-1,2,3,6-tetra-hydropyridine·HCl, and 90.0 kg of acetonitrile. The mixture is agitated and cooled to 5°–10° C., and 4.6 kg (45.5 mol) of triethylamine is charged using a metering pump at a rate of about 0.3 kg/minute. The batch temperature is maintained at 15°–20° C. The mixture in the still is agitated for at least 6 hours and is allowed to warm to ambient temperature.

A 200 L reactor is charged with 60.0 L of water and 4.0 kg (47.6 mol) of sodium bicarbonate, and the agitator is started. The aqueous sodium bicarbonate solution is transferred from the reactor to the still. The still is charged with 80 L of water followed by 90.0 L of toluene. The mixture in the still is agitated for at least 30 minutes, and the phases are allowed to separate. The lower aqueous phase in the still is drained to the reactor. The still is charged with 50.0 kg of water. The mixture in the still is agitated for at least 30 minutes, and the phases are allowed to separate. The lower aqueous phase in the still is drained to the reactor. Toluene (30.0 L) is charged to the reactor, the mixture in the reactor is agitated for 30 minutes, and the phases are allowed to separate. The lower aqueous phase is discarded to the chemical waste system. The toluene phase in the reactor is transferred to the still. The reactor is charged with 50 L of water and 6.8 kg (65.7 mol) of hydrochloric acid 37% CP. The aqueous hydrochloric acid is transferred from the reactor to the 400 L still. The aqueous hydrochloric acid extract is drained to the chemical waste system. The reactor is charged with 40.0 L of water and 4.0 kg of sodium chloride. The aqueous sodium chloride solution is transferred from the reactor to the still, the mixture in the still is agitated for 20 minutes, and the phases allowed to separate. The lower aqueous phase in the still is discarded to the chemical waste system. The upper toluene phase containing product in the 400 L still is transferred to the 200 L still (convenience in the distillation). The 200 L still is set for vacuum distillation into the 200 L reactor. The condenser Heat Transfer Medium (HTM) temperature is set at 5°–10° C., and the solution is concentrated to a volume of 20±5 L. The batch temperature is maintained below 60° C. The distillate is discarded. The still is charged with 30 kg of ethyl alcohol 2B. The solution in the still is cooled to 0°±5° C. and held there for at least 2 hours. The solid product from the still is filtered on a centrifuge directing the filtrate to the reactor. The alcohol/toluene wet product is placed in a vacuum tray dryer and dried at 40°±5° C. for at least 24 hours using the best available vacuum. The filtrate is transferred from the reactor to the still. The still is set for vacuum distillation into the reactor. The filtrate is concentrated to 5±5 L. This solution is transferred to a 20 L bottle. The distillate is discarded. The concentrated filtrate is cooled at 0°+5° C. for 24 to 48 hours. The solid product is filtered on a Buchner funnel. The alcohol/toluene wet product is transferred to a vacuum tray dryer and dried at 40°+5° C. for at least 24 hours using best available vacuum. The dry product is transferred to plastic lined drums and stored in a dry area at a temperature below 35° C.

The yield is 8.4 kg of first crop and 0.6 kg of second crop.

The product, (S) 1,2,3,6-tetrahydro-1-[(5-oxo-3-phenyl-3-cyclohexenyl)carbonyl]-4-phenylpyridine is an off-white to pale yellow solid; mp 137°–141° C. (uncorrected).

200 MHz $^1$H NMR (CDCl$_3$): $\delta$2.62 (m, 2H), 2.89 (m, 2H), 3.00 (m, 1H), 3.74 (m, 1H), 3.88 (m, 1H), 3.91 (m, 1H), 4.30 (m, 2H), 6.04 (m, 2H), 6.14 (s, 1H), 7.23–7.60 (m, 10H).

Method B (S)5-Oxo-3-phenyl-3-cyclohexenecarboxylic acid, 24.0 kg (111.1 mol) is charged to a 200 L still with 150.0 kg acetonitrile. To a separate reactor is charged 20.0 kg (123.5 mol) of carbonyl diimidazole and 100.0 kg of acetonitrile. The solution in the reactor is cooled to 20°±5° C. The carbonyl diimidazole solution is slowly transferred from the reactor to the still. The batch temperature in the still is maintained at 25°±5° C. The reactor is charged with 50.0 kg of acetonitrile and the wash is transferred from the reactor to the still. The temperature of the mixture in the still is maintained for 3 to 4 hours at 20°–30° C. The mixture in the still is cooled to 10°–15° C. with agitation. The still is charged with 18.0 kg (112.9 mol) of 4-phenyl-1,2,3,6-tetrahydropyridine, and the batch temperature is maintained at 20°–25° C. The transfer hoses are washed with 50.0 kg of acetonitrile, and the wash is directed to the still. The still is charged with 12.0 kg (118.6 mol) of triethylamine using a metering pump at a rate of about 1.0 kg/minute. The batch temperature is maintained at 20°–25° C. (If 4-phenyl-1,2,3,6-tetrahydropyridine-hydrochloride is used, 24 kg of triethylamine will be charged.) The mixture in the still is agitated for at least 6 hours. The temperature of the contents of the still are allowed to warm to ambient temperature. The reactor is charged with 500 L of water and 10 kg (119 mol) of sodium bicarbonate is charged to a reactor, and the mixture is agitated. The aqueous sodium bicarbonate solution from the reactor is slowly charged to the still. The still is charged with 500 L of toluene. The mixture in the still is agitated for about 30 minutes, and the phases are allowed to separate. The lower aqueous phase in the still is transferred to the reactor. The still is charged with 200 L of water. The mixture in the still is agitated for at least 15 minutes and the phases allowed to separate. The lower aqueous phase in the still is transferred to the reactor. The reactor is charged with 100 L of toluene. The mixture in the reactor is agitated for about 15 minutes and the phases allowed to separate. The lower aqueous phase in the reactor is discarded. The upper toluene phase in the reactor is transferred to a still. The reactor is charged with 300 L of water, 12 kg of hydrochloric acid 37% CP, and the mixture is agitated. The aqueous hydrochloric acid is slowly transferred from the reactor to the still with agitation. The mixture in the still is agitated for at least 15 minutes and the phases allowed to separate. The lower aqueous phase in the still is discarded. The reactor is charged with 300 L of water and 20 kg of sodium chloride. The aqueous sodium chloride from the reactor is transferred into the still, and the mixture agitated for about 20 minutes and the phases allowed to separate. The lower aqueous phase in the still is discarded. The upper toluene phase containing product in the still is transferred in portions to a smaller still for vacuum distillation. The smaller still is set for vacuum distillation, and the solution is concentrated to a volume of about 60±5 L. The batch temperature is maintained below 65° C. The distillate is discarded. The still is charged with 120 kg of ethyl alcohol, 2B. The solution in the still is cooled to 0°±5° C. and held for at least 2 hours. The solid product from the still is filtered onto a centrifuge. The filtrate is directed to a reactor. The still is charged with 50 kg of ethyl alcohol, 2B. The mixture in the still is agitated for at least 10 minutes, and the wash is transferred from the still onto the cake on the centrifuge. The filtrate is directed to a reactor. The solid product on the centrifuge is transferred to drying trays and dried in vacuo, if desired. The product is usually carried into the next step wet. The filtrates are transferred from the reactor to a still. The contents of the still are vacuum distilled maintaining the batch temperature below 60° C. The contents are distilled to a volume of 50±10 L. The distillate is discarded. The solution in the still is cooled to 0°±5° C. for at least 2 hours. The solid product from the still is filtered onto a centrifuge. The filtrate is directed to a reactor. The still is charged with 30 kg of ethyl alcohol, 2B. The mixture in the still is agitated for at least 10 minutes, and the wash from the still is transferred onto the cake on the centrifuge. The filtrates are discarded. The solid product on the centrifuge is transferred to drying trays and dried in vacuo, if desired. The product is usually carried into the next step wet.

Step C

Preparation of (S)1,2,3,6-Tetrahydro-1-[(5-hydroxy-3-phenyl-3-cyclohexenyl)carbonyl]-4-phenylpyridine (S)1,2,3,6-Tetrahydro-1-[(5-oxo-3-phenyl-3-cyclohexenyl)carbonyl]-4-phenylpyridine, 8.4 kg (23.5 mol), is charged to a 200 L still with 30 kg of ethanol, 2B. The mixture in the still is cooled to 15°±5° C. Sodium borohydride, 1.2 kg (32.4 mol) and 30 kg of ethanol, 2B is charged to a reactor. The contents of the reactor are transferred to the still. The batch temperature in the still is maintained at 20°±5° C. The solution in the reactor is transferred to the still and maintained at 20°±5° C. The reactor is charged with 15 kg of ethanol, 2B. The ethanol in the reactor is agitated for at least 3 minutes and transferred to the still. The suspension in the still is agitated for at least 12 hours. The batch temperature in the still is warmed to 25°±5° C. The mixture in the still is cooled to 10°±5° C. The reactor is charged with 30 L of water and 5 kg (92.5 mol) of ammonium chloride. The ammonium chloride solution is transferred from the reactor to the still using a metering pump at a rate of about 0.3 L/minute. If foaming occurs, stop or slow the addition until the foam subsides. The solution in the still is cooled under nitrogen to 0°±5° C. for at least 2 hours. The solid product from the still is filtered onto a centrifuge. The filtrates are discarded. The wet product is transferred to vacuum tray driers and dried at 40°±5° C. for at least 24 hours using the best available vacuum.

The yield of (S)1,2,3,6-tetrahydro-1-[(5-hydroxy-3-phenyl-3-cyclohexenyl)carbonyl]-4-phenylpyridine is 6.38 kg of first crop and 0.3 kg of second crop of white to light yellow solid; mp 162°–167° C. (uncorrected).

200 MHz $^1$H NMR (CDCl$_3$): δ1.75 (m, 2H), 2.62 (m, 2H), 3.16 (m, 1H), 3.21 (m, 2H), 3.73 (m, 2H), 3.79 (m, 1H), 4.25 (m, 2H), 4.28 (m, 1H), 6.03 (s, 1H), 6.17 (m, 1H), 7.26–7.42 (m, 10H).

ASSAY (HPLC): 96.2% by area (major isomer) and 1.7% by area (minor isomer).

| HPLC Conditions: | |
| --- | --- |
| Column: | YMC-AQ, C$_{18}$ 5 µm, 250 × 4.6 mm |
| Flow Rate: | 1.5 mL/minute |
| Mobile Phase: | 600 CH$_3$CN/400 solution A* (v/v) |
| Wavelength: | 214 nm |
| Injection Volume: | 20 µL |
| Sample Conc.: | ~5.0 mg/25 mL in mobile phase |

*Solution A: Dissolve 5.75 g NH$_4$H$_2$PO$_4$ in 1 L HPLC grade water, add 6 mL triethylamine, and adjust the pH of the solution to 3.0 using 85% H$_3$PO$_4$.

Step D

Preparation of R(+)1,2,3,6-Tetrahydro-4-phenyl-1-[(3-phenyl-3-cyclohexenyl)carbonyl]pyridine A scrubber is charged with 750 L of tap water and 300 kg of sodium hydroxide, 50%. This must be connected to each piece of equipment in order to remove any hydrogen cyanide evolved in the process for safety purposes.

A 400 L still is charged with 8.4 kg (23.4 mol) of (S)1,2,3,6-tetrahydro-1-[(5-hydroxy-3-phenyl-3-cyclohexenyl)carbonyl]-4-phenylpyridine, 3.8 kg (27.9 mol) of zinc chloride, 3.5 kg (55.7 mol) of sodium cyanoborohydride, and 70 kg of heptane. The mixture in the still is agitated. A 80 L reactor is charged with 15 kg of tetrahydrofuran and 5 kg (83.3 mol) of glacial acetic acid. The batch temperature in the still is maintained at 25°±5° C. The solution of glacial acetic acid in tetrahydrofuran is transferred from the reactor to the still. The mixture in the still is agitated for at least 6 hours at 25°±5° C. The 80 L reactor is charged with 30 L of water and 5.3 kg (99 mol) of ammonium chloride, and the agitator is started.

The aqueous ammonium chloride is transferred from the reactor to the still using a metering pump at a rate of about 1 L/minute. The batch temperature is maintained at 20°±5° C. The mixture in the still is agitated for at least 30 minutes. The reactor is charged with 20 L of water and 3.6 kg (34.8 mol) of concentrated hydrochloric acid, 37% aqueous solution.

The aqueous hydrochloric acid is transferred from the reactor to the still using a metering pump at a rate of about 0.5 L/minute. The batch temperature is maintained at 20°±5° C. The mixture in the still is agitated for at least 2 hours.

The still is set for vacuum distillation using a vacuum scrubber system. The solution is concentrated to a volume of approximately 350±50 L. The batch temperature is maintained below 50° C. The heptane/tetrahydrofuran distillate is discarded. A reactor is charged with 200 L of water.

NOTE: The filtrate contains hydrogen cyanide and vapors may contain hydrogen cyanide.

A sealed filter dryer is pressure tested at 15 pounds per square inch gauge (psig) with nitrogen before use. Any drop in pressure may not exceed 1 psig over a 15-minute period. Otherwise, fix the leaks and retest. The product from the still is filtered onto the sealed filter dryer, diverting the filtrate into a reactor. The still is charged with 600 L of tetrahydrofuran. The contents of the still are agitated and heated to 40°±5° C. About 300 L of the warm tetrahydrofuran solution in the still is transferred to the sealed filter. The contents of the sealed filter are re-slurried and heated to 40°±5° C. using about 50° C. tempered water on the jacket. The contents are agitated and held at this temperature for at least 30 minutes.

A Pall filter is installed at the intake valve of a still to remove any fine particulate matter. The warm tetrahydrofuran with dissolved product in the sealed filter is transferred through the Pall filter to a still. The rest of the warm tetrahydrofuran solution in the first still is transferred to the sealed filter. The contents of the sealed filter are re-slurried and heated to 40°±5° C. using about 50° C. tempered water on the jacket. The mixture is agitated and held at this temperature for at least 30 minutes. The warm tetrahydrofuran with dissolved product from the sealed filter is transferred through the Pall filter into the still. The sealed filter is rinsed using the spray nozzles with 50 L of tetrahydrofuran. The rinse is directed through the Pall filter and transfer line into the still. The still, containing the tetrahydrofuran solution of product, is set for vacuum distillation using the vacuum scrubber system. The solution is concentrated to a volume of approximately 60±20 L. The batch temperature is maintained below 50° C. The still, containing the concentrated solution of the product, is charged with 150 kg of absolute ethanol. The still is set for vacuum distillation. The solution is concentrated to a volume of approximately 60±20

L. The batch temperature is maintained below 50° C. The still is charged with 300 kg of absolute ethanol. The tetrahydrofuran/ethanol distillate is discarded. The mixture in the still is agitated for about 1 hour at 75°±5° C. The solution in the still is cooled under nitrogen to 0°±5° C. and held for at least 2 hours. The solid product in the still is filtered onto a centrifuge. The filtrate is directed to a 80 L reactor. The still is charged with 15 kg of ethyl alcohol, 2B. The mixture in the still is agitated for at least 3 minutes, and the wash is transferred from the still to the centrifuge while directing the filtrate to the 80 L reactor. The filtrates from the reactor are transferred to the 200 L still. The still is set for vacuum distillation. The solution is concentrated to a volume of approximately 15±5 L. The batch temperature is maintained below 40°±5° C. The solution is transferred to a 20 L bottle. The bottle and contents are cooled to 0°±5° C. The resulting solid is filtered on a Buchner funnel. The wet product is transferred to a vacuum tray dryer and dried at 40°±5° C. for at least 24 hours using best available vacuum.

The yield of R(+)1,2,3,6-tetrahydro-4-phenyl-1-[(3-phenyl-3-cyclohexenyl)carbonyl]pyridine is 4 kg as a first crop and 0.5 kg as a second crop of white to light yellow solid; mp 142°–147° C. (uncorrected).

200 MHz $^1$H NMR (CDCl$_3$): δ1.91 (m, 2H), 2.37 (m, 2H), 2.52–2.61 (m, 1H), 3.77 (m, 2H), 3.88 (s, 1H), 4.24 (m, 2H), 5.29 (m, 2H), 6.04 (s, 1H), 6.14 (m, 2H), 7.23–7.42 (m, 10H).

Step E

Preparation of R(+)1,2,3,6-Tetrahydro-4-phenyl-1-[(3-phenyl-3-cyclohexen-1-yl)methyl]pyridine A drum of absolute ethanol is placed in a cold room for use as washes. A 200 L still is charged with 4.0 kg (11.64 mol) of R(+)1,2,3,6-tetrahydro-4-phenyl-1-[(3-phenyl-3-cyclohexenyl)carbonyl]pyridine. That still is charged with 44.4 kg of dry tert-butyl methyl ether (containing <0.02% water).

The still is charged with 16.6 kg (18 mol) of a solution of lithium aluminum hydride, 1M in tetrahydrofuran, using a flow rate of 0.1 to 0.5 kg/minute and less than 12 psi argon pressure. The batch temperature is maintained at 30°–45° C. This reaction has been run successfully between 0° C. and reflux ~66° C. For best results, stop the addition if the temperature rises above 45° C. Cool to <45° C. and resume addition.

When addition is complete, rinse the lithium aluminum hydride discharge line with approximately 5 kg of tetrahydrofuran. Add the rinse to the still. The mixture in the still is agitated at 30°–45° C. for 3 to 4 hours. The mixture in the still is cooled to 20°–25° C. A solution of 1.27 kg of water in 4.4 kg of tetrahydrofuran is prepared in a glass bottle in a metal can. The solution of 1.27 kg of water in 4.4 kg of tetrahydrofuran is charged to the still using a metering pump starting at a rate of 0.05–0.1 L per hour until the frothing subsides, then the addition of the entire solution is completed at a rate of 0.1–0.5 L per hour. A saturated solution of sodium sulfate in water is prepared by mixing 1 kg of sodium sulfate in 5 kg of water in a glass bottle in a metal can. If there is no undissolved sodium sulfate, add more until some remains undissolved. The still is charged with 4 kg of the saturated sodium sulfate solution using a metering pump at a rate of 0.1–0.5 L per hour. The temperature of the contents of the still is heated to 40°–45° C. The slurry of inorganics in the still is filtered through a filter, and the filtrate is directed into a 400 L reactor. The still is charged with 20 L of tetrahydrofuran (as a wash), and the wash is warmed to 40°–45° C. The wash in the still is transferred through a filter into the 400 L reactor. The temperature of the product solution in the reactor is maintained at 40°–45° C.

The solution of the product is transferred to a still, and most of the solvent is removed by vacuum distillation. Absolute ethanol is added, and most of the solvent is removed by vacuum distillation. Absolute ethanol is added, and the solution is cooled to –10° C. to 0° C. for 1 to 2 hours, and the R(+)1,2,3,6-tetrahydro-4-phenyl-1-[(3-phenyl-3-cyclohexen-1-yl)methyl]pyridine is isolated by centrifugation. The product cake is washed with cold absolute ethanol and vacuum dried. Storage is in the same manner as the maleate salt.

Step F

Preparation of R(+)1,2,3,6-Tetrahydro-4-phenyl-1-[(3-phenyl-3-cyclohexen-1-yl)methyl]pyridine Maleate A tetrahydrofuran solution of the product from Step E is transferred to a still and vacuum distilled. The contents of the still are maintained at 25°–75° C. The still is charged with 100 L of absolute ethanol and most of the ethanol/tetrahydrofuran is vacuum distilled. The contents of the still are maintained at 25°–75° C. The still is charged with 100 L of absolute ethanol, and most of the ethanol/tetrahydrofuran is vacuum distilled. The contents of the still are maintained at 25°–75° C. The still is charged with 75 L of absolute ethanol, and the mixture is heated to a gentle reflux. A 200 L reactor is charged with 1.74 kg (15 mol) of maleic acid and 15.8 kg of absolute ethanol. The resulting slurry is agitated in the reactor, and the temperature of the contents is maintained at 60°–65° C. The ethanol solution of the product is added to the maleic acid solution or alternatively the maleic acid solution is added to the ethanol solution of the product in the 400 L reactor, and an argon purge is established on the reactor.

The contents of the reactor are maintained at 50°–55° C. and agitated for 1 to 2 hours. The inorganics in the filter are discarded. Seeds of high quality product are added, if needed, to the reactor.

The contents of the reactor are cooled to 35°–40° C. and agitated for 1 to 2 hours. The contents of the reactor are cooled to –10° C. to –5° C. and agitated for 1 to 2 hours. The solid product is filtered onto a centrifuge, and the filtrate is directed to a 400 L reactor. The reactor is charged with 15.8 kg of cold absolute ethanol and directed onto the cake on the centrifuge. The filtrate is directed to the 400 L reactor. The ethanol wet product is transferred to a vacuum tray dryer and dried at 30°±5° C. for at least 24 hours using best available vacuum.

The dry product is transferred to polyethylene double-lined plastic bags in moisture proof drums wearing an air-line supplied respirator. Store the product below 35° C. in a dry storage area.

Second Crop

The filtrates in the reactor are transferred to a still. The filtrates are vacuum distilled until the solution is below the agitator. The still is charged with sufficient absolute ethanol to allow agitation and the contents are cooled to –10°0 to –5° C. The distillate is discarded. The solid product from the still is filtered onto the centrifuge, and the filtrate is discarded. The 200 L reactor is charged with 8 kg of cold absolute ethanol. This wash is directed onto the cake on the centrifuge, and the filtrate is discarded. The ethanol wet product is transferred to a vacuum tray dryer and dried at 30°±5° C. for at least 24 hours using best available vacuum.

The dry product is transferred to polyethylene double-lined plastic bags in moisture proof drums. The product is stored below 35° in a dry storage area.

The yield of R(+)1,2,3,6-tetrahydro-4-phenyl-1-(3-phenyl-3-cyclohexen-1-yl)methylpyridine maleate is 3.6 kg as a first crop and 0.6 kg as a second crop of white to off-white solid;

200 MHz $^1$H NMR (CDCl$_3$): δ1.65–1.80 (m, 1H), 1.93–2.05 (m, 1H), 2.05–2.25 (m, 4H), 2.25–4.20 (m, 9H), 6.0 (m, H), 6.08 (m, 1H), 6.15 (ss, 2H), 7.15–7.45 (m, 10H); acid protons of maleic acid not observed.

|  | Retention Time (min) | Area % |
|---|---|---|
| Assay (HPLC) (Area %): HPLC: |  |  |
| Not less than 98% | 23.2 | 99.52 |
| Impurities (HPLC Area %): |  |  |
| Not more than 0.5% each | 6.50 | .04 |
|  | 6.90 | .28 |
|  | 9.40 | .01 |
|  | 11.50 | .06 |
|  | 18.50 | .07 |
|  | 21.00 | .01 |
|  | 21.00 | .01 |

Total Impurities: 0.48% Not more than 2.0%

| HPLC Conditions |  |
|---|---|
| Column: | YMC-AQ, C18, 5 µm, 250 × 4.6 mm |
| Flow Rate: | 1.5 mL/minute |
| Mobile Phase: | 350 CH$_3$CN/650 solution A* (v/v) |
| Wavelength: | 214 nm |
| Injection Volume: | 20 µL |
| Sample Conc.: | ~5.0 mg/25 mL in mobile phase |

*Solution A: Dissolve 5.75 g NH$_4$H$_2$PO$_4$ 1 L HPLC grade water, add 6 mL triethylamine, and adjust the pH of solution to 3.0 using 85% H$_3$PO$_4$ Titration for Maleic Acid: 26.00% (Avg. of 2 values) Theoretical=26.05%

Specific Rotation: $[\alpha]_D^{25}$=+62.46° 1% in methanol (Avg. of 6 values)

| Chiral HPLC Ratio: HPLC: | Retention Time (min) | Area % Ratio |
|---|---|---|
| Enantiomer; (Limit of Detection 0.03%) | 12.6 | ND (–) |
|  | 33.2 | 99.96% |
| Conditions: |  |  |
| Column: | Chiralcel OJ, 250 × 4.6 mm |  |
| Flow Rate: | 1.0 mL/minute |  |
| Mobile Phase: | 700 hexane/300 isopropanol (IPA) (v/v) |  |
| Wavelength: | 254 nm |  |
| Injection Volume: | 20 µL |  |
| Sample Conc.: | ~10.0 mg/25 mL in IPA (sonicated until it is dissolved) |  |

PREPARATION OF STARTING MATERIALS

EXAMPLE A

5-Oxo-3-phenyl-3-cyclohexenecarboxylic Acid

An 800 L still is charged with 53.9 kg (306 mol) of 3-benzoylacrylic acid. The 800 n still is charged with 41 kg (315 mol) of ethyl acetoacetate. The still is charged with 150 L of water. The agitator is started on the still. The still is charged with 56 kg (1475 mol) of 50% sodium hydroxide, followed by 20 L of water. The resulting solution is agitated, and the temperature of the contents is maintained at 45°–50° C. for 16 to 18 hours after the addition of the sodium hydroxide. The solution in the still is then refluxed for 20 to 24 hours (~100° C.). An 800 L reactor is charged with 140 L of water and 90.6 kg (1100 mol) of concentrated hydrochloric acid followed by 20 L of water, and the agitator is started. The reaction mixture in the still is cooled to 25°–40° C. The still is vented through the condenser to an atmospheric scrubber. The cooled solution in the still (25°–40° C.) is added to the diluted hydrochloric acid solution in the reactor at a rate of about 2–4 L/minute. The still is charged with 100 L of water, and this is transferred to the reactor. The resulting slurry in the reactor is agitated at 25°–40° C. for about 2 to 4 hours. The solid product in the reactor is filtered onto a centrifuge. The reactor is charged with 100 L water, and the water is directed to the cake on the centrifuge. The mother liquors and washes are discarded. The still is charged with 100 L water, the water is directed over the filter-cake, and the filtrate is discarded. The product wet cake from the centrifuge is returned to the still followed by 400 L of water, and the slurry is agitated for 2 to 4 hours. The solid product is filtered onto a centrifuge. The still and filter-cake are washed with 200 L of water. The filtrates are discarded. The water wet 5-oxo-3-phenyl-3-cyclohexenecarboxylic acid is transferred to a vacuum tray dryer and dried at 80°±5° C. for at least 24 hours using the best available vacuum to yield 62.5 kg of an off-white to pale yellow solid; mp 140°–160° C. (average of 2 determinations). The dry product is stored in plastic lined drums.

200 MHz $^1$H NMR (CDCl$_3$): δ2.3–2.95 (m, 4H), 2.96–3.45 (m, 3H), 6.45 (s, 1H), 7.25–7.65 (m, 5H), 10.0–10.8 (br.s, 1H).

EXAMPLE B n-Butyl 5-Oxo-3-phenyl-3-cyclohexenecarboxylate

A mixture of 5-oxo-3-phenyl-3-cyclohexene-carboxylic acid (Example A) (216 g) and n-butyl alcohol (500 g) is treated with concentrated sulfuric acid (10 mL) with agitation. The mixture is stored at ambient temperature for 18 hours, heated to 50°–55° C. for 1 to 2 hours, and allowed to cool. The solution is concentrated under vacuum to an oil. The oil is poured into an excess of saturated sodium carbonate and extracted into toluene. The toluene extract is passed over a pad of silica gel and concentrated at reduced pressure at a temperature of 90°–95° C. The product is an oil; bp 150°–155° C. at 0.01 mm Hg. HPLC purity=96.9% with the reminder being toluene.

200 MHz $^1$H NMR (CDCl$_3$): δ0.87–1.1 (t, 3H), 1.1–1.8 (complex multiplet, 4H), 2.5–3.2 (complex multiplet, 5H), 4.0–4.15 (t, 2H), 6.3–6.5 (s, 1H), 7.2–7.7 (complex multiplet, 5H).

We claim:

1. A process for the preparation of the compound of Formula I

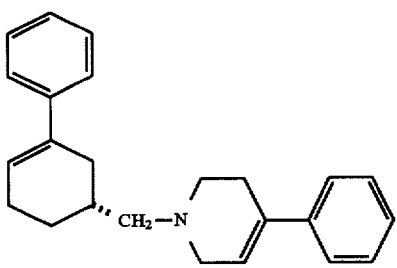
I and pharmaceutically acceptable salts thereof which comprises:

Step (a) treating the racemic compound of Formula VIII

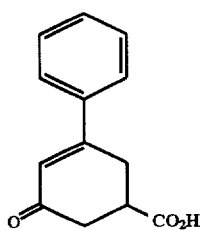
VIII with cinchonidine in a solvent to afford the compound of Formula VII

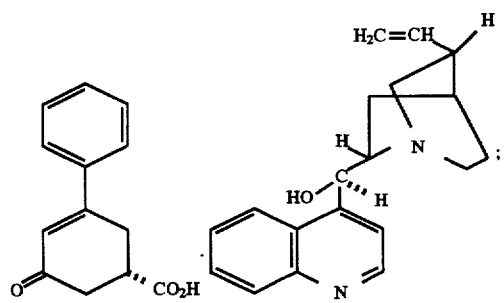
VII

Step (b) treating the compound of Formula VII with a base in a solvent to afford after acidification the compound of Formula VI

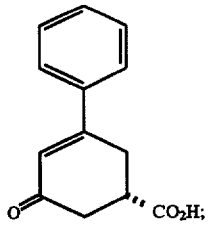
VI

Step (c) treating the compound of Formula VI with the compound of Formula V

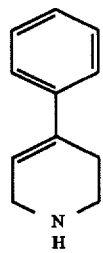
V in the presence of a coupling reagent and a solvent to afford the compound of Formula IV

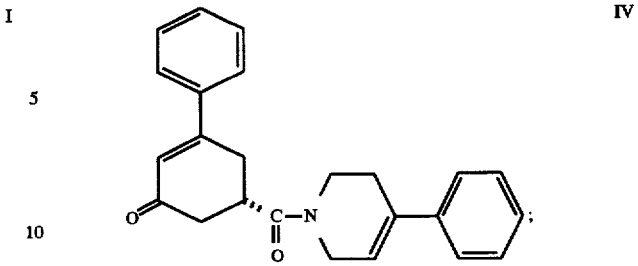
IV

Step (d) treating the compound of Formula IV with a reducing reagent in a solvent to afford a mixture of compounds of Formula IIIa and Formula IIIb IIIa IIIb Step (e) treating the mixture of compounds of Formula IIIa and Formula IIIb with a mixture of zinc chloride, and sodium cyanoborohydride in a solvent followed by a solution of a carboxylic acid in a solvent to afford the compound of Formula II

II

Step (f) treating the compound of Formula II with a metal hydride reducing agent in a solvent to afford the compound of Formula I;

Step (g) and, if desired, converting the resulting compound of Formula I to a corresponding pharmaceutically acceptable acid addition salt by conventional means, and if so desired, converting the corresponding pharmaceutically acceptable acid addition salt to a compound of Formula I by conventional means.

2. A process according to claim 1 wherein the solvent in Step (a) is an alcohol.

3. A process according to claim 2 wherein the solvent is isopropanol.

4. A process according to claim 1 wherein the base in Step (b) is an alkali metal hydroxide.

5. A process according to claim 4 wherein the base is sodium hydroxide.

6. A process according to claim 1 wherein the solvent in Step (b) is methanol.

7. A process according to claim 1 wherein the coupling reagent in Step (c) is selected from the group consisting of: carbonyl diimidazole; and 1-(3-dimethylaminopropyl)-3-ethylcarbodiimide, 1-hydroxybenzotriazole hydrate, and triethylamine.

8. A process according to claim 7 wherein the coupling reagent is carbonyl diimidazole.

9. A process according to claim 1 wherein the solvent in Step (c) is selected from the group consisting of: acetonitrile; and tetrahydrofuran.

10. A process according to claim 9 wherein the solvent is acetonitrile.

11. A process according to claim 1 wherein the reducing reagent in Step (d) is a cation borohydride.

12. A process according to claim 11 wherein the reducing reagent is sodium borohydride.

13. A process according to claim 1 wherein the solvent in Step (d) is selected from the group consisting of: an alcohol; and an aqueous alcohol.

14. A process according to claim 13 wherein the solvent is ethanol.

15. A process according to claim 1 wherein the solvent in Step (e) is selected from the group consisting of: hexane; and heptane.

16. A process according to claim 15 wherein the solvent is heptane.

17. A process according to claim 1 wherein the carboxylic acid in Step (e) is selected from the group consisting of: glacial acetic acid; propanoic acid; butyric acid; and pivalic acid.

18. A process according to claim 17 wherein the carboxylic acid is glacial acetic acid.

19. A process according to claim 1 wherein the carboxylic acid in Step (e) is added as a solution in a solvent selected from the group consisting of: hexane; heptane; and tetrahydrofuran.

20. A process according to claim 19 wherein the solvent is tetrahydrofuran.

21. A process according to claim 1 wherein the metal hydride reducing agent in Step (f) is lithium aluminum hydride.

22. A process according to claim 1 wherein the solvent in Step (f) is tetrahydrofuran.

23. A process according to claim 1 wherein the compound of Formula I is R(+)1,2,3,6-tetrahydro-4-phenyl-1-[(3-phenyl-3-cyclohexen-1-yl)methyl]-pyridine maleate.

24. A process for the preparation of the compound of Formula VI

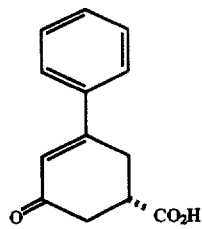

VI which comprises:

Step (a) treating the racemic compound of Formula VIII

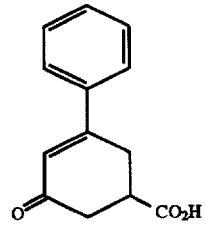

VIII with cinchonidine in a solvent to afford the compound of Formula VII

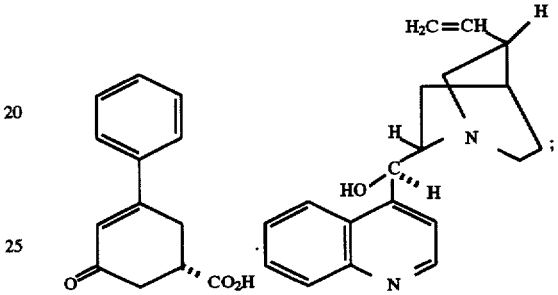

VII and

Step (b) treating the compound of Formula VII with a base in a solvent to afford after acidification the compound of Formula VI.

25. A process according to claim 24 wherein the solvent in Step (a) is an alcohol.

26. A process according to claim 25 wherein the solvent is isopropanol.

27. A process according to claim 24 wherein the base in Step (b) is an alkali metal hydroxide.

28. A process according to claim 27 wherein the base is sodium hydroxide.

29. A process according to claim 24 wherein the solvent in Step (b) is methanol.

30. A process for the preparation of the compound of Formula VI

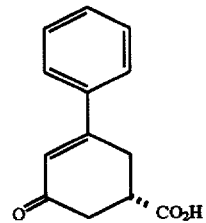

VI which comprises treating the racemic compound of Formula IX

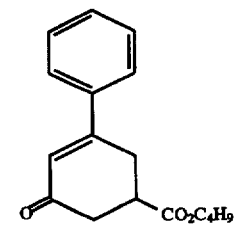

IX in a solvent at about pH 5 with α-chymotrypsin to afford after separation of unreacted ester and acidification the compound of Formula VI.

31. A process according to claim 30 wherein the solvent is water.

32. A process for the preparation of the compound of Formula II

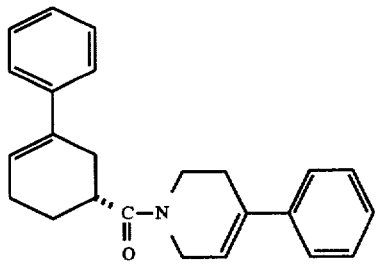

which comprises:

Step (a) treating the racemic compound of Formula VIII

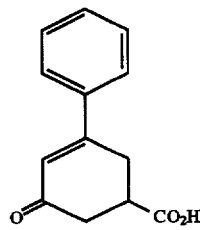

with cinchonidine in a solvent to afford the compound of Formula VII

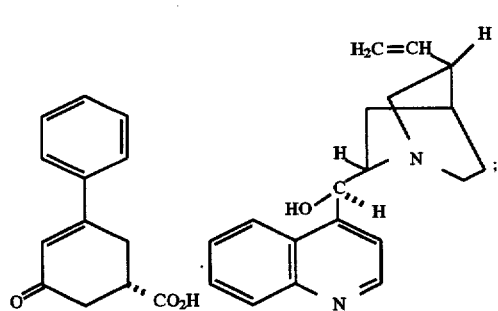

Step (b) treating the compound of Formula VII with a base in a solvent to afford after acidification the compound of Formula VI

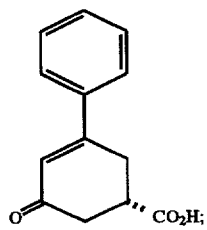

Step (c) treating the compound of Formula VI with the compound of Formula V

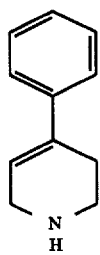

in the presence of a coupling reagent and a solvent to afford the compound of Formula IV

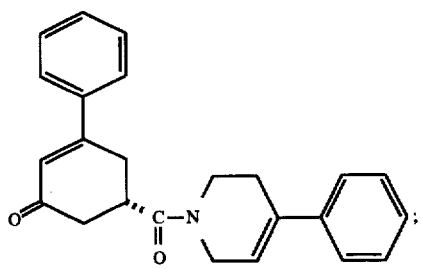

Step (d) treating the compound of Formula IV with a reducing reagent in a solvent to afford a mixture of compounds of Formula IIIa and Formula IIIb

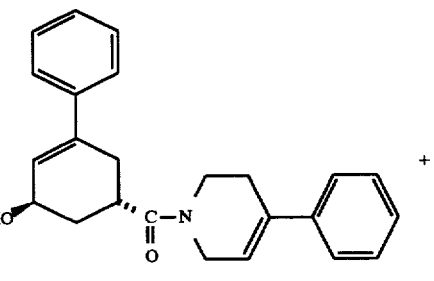

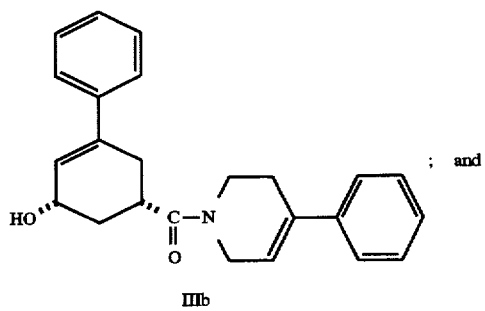

Step (e) treating the mixture of compounds of Formula IIIa and Formula IIIb with a mixture of zinc chloride, and sodium cyanoborohydride in a solvent followed by a solution of a carboxylic acid in a solvent to afford the compound of Formula II.

33. A process for the preparation of the compounds of Formula IIIa and Formula IIIb

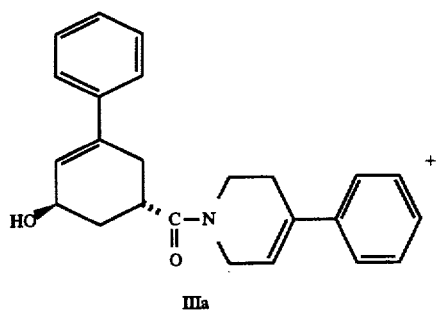

IIIa

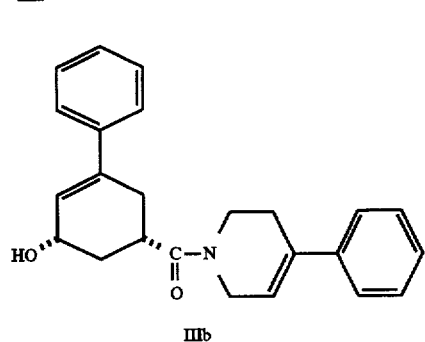

IIIb which comprises:

Step (a) treating the racemic compound of Formula VIII

VIII

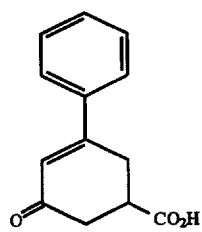

with cinchonidine in a solvent to afford the compound of Formula VII

VII

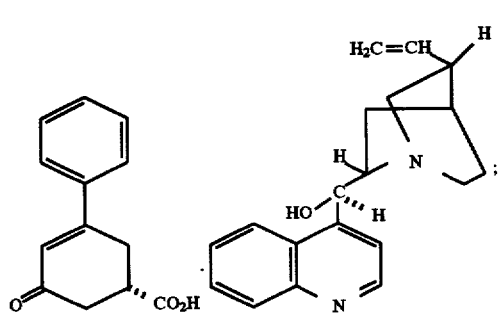

Step (b) treating the compound of Formula VII with a base in a solvent to afford after acidification the compound of Formula VI

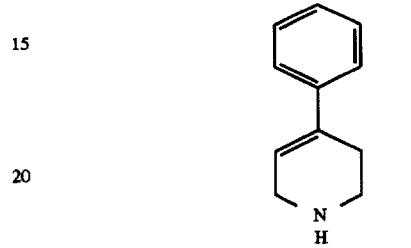

VI

Step (c) treating the compound of Formula VI with the compound of Formula V

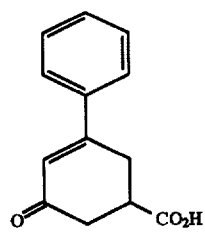

V in the presence of a coupling reagent and a solvent to afford the compound of Formula IV

IV

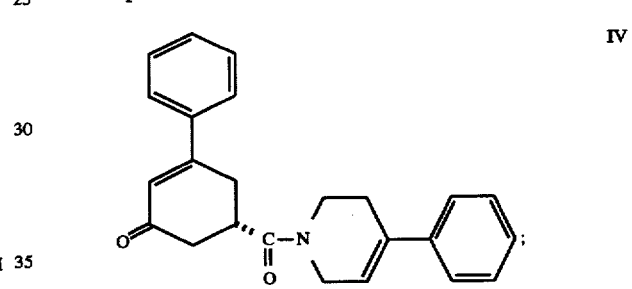

and

Step (d) treating the compound of Formula IV with a reducing reagent in a solvent to afford a mixture of compounds of Formula IIIa and Formula IIIb.

34. A process for the preparation of the compound of Formula IV

IV

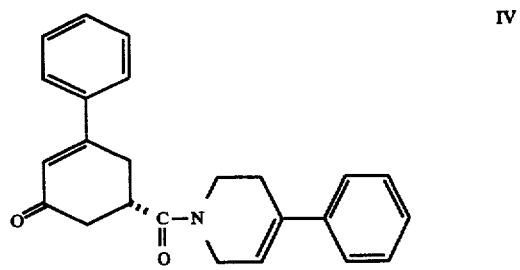

which comprises:

Step (a) treating the racemic compound of Formula VIII

VIII with cinchonidine in a solvent to afford the compound of Formula VII

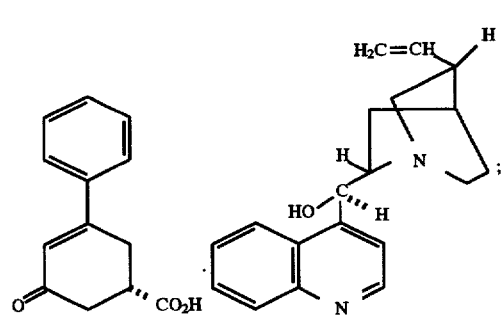

Step (b) treating the compound of Formula VII with a base in a solvent to afford after acidification the compound of Formula VI

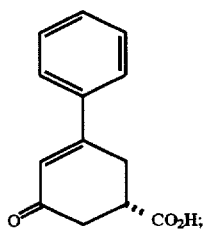

and

Step (c) treating the compound of Formula VI with the compound of Formula V

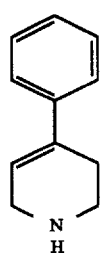

in the presence of a coupling reagent and a solvent to afford the compound of Formula IV.

35. The compound of Formula IX

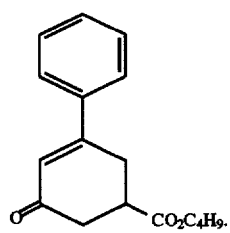

36. A compound selected from the group consisting of Formula IIIa and Formula IIIb

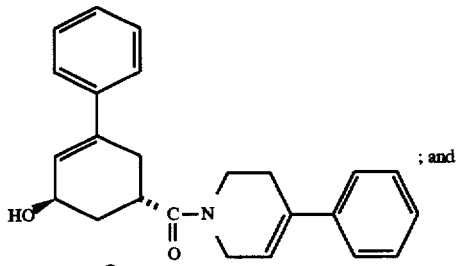

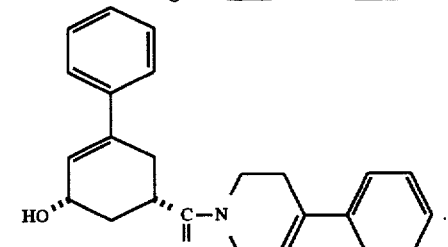

37. The compound of Formula IV

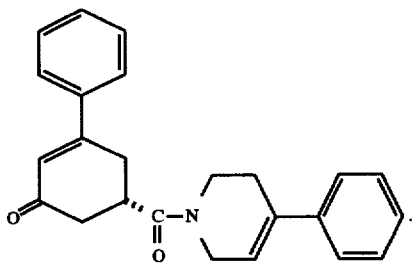

38. The optically pure compound of Formula VI

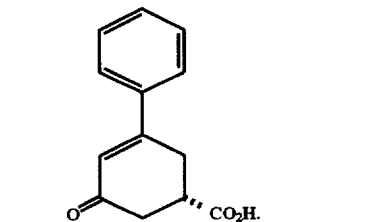

39. The compound of Formula VII

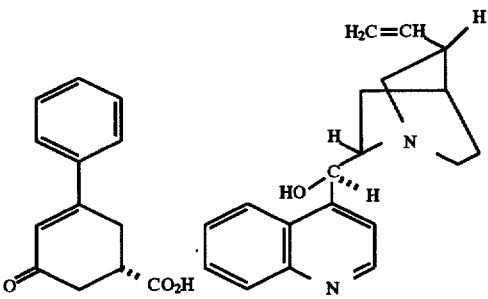

* * * * *